[54] ASYMMETRIC PROCESS FOR PREPARING FLORFENICOL, THIAMPHENICOL CHLORAMPHENICOL AND OXAZOLINE INTERMEDIATES

[75] Inventors: Guang-Zhong Wu, Somerville; Wanda I. Tormos, Elizabeth, both of N.J.

[73] Assignee: Schering Corporation, Kenilworth, N.J.

[21] Appl. No.: 993,932

[22] Filed: Dec. 18, 1992

[51] Int. Cl.$^5$ .................. C07C 233/05; C07C 233/12; C07D 263/08; C07D 301/19

[52] U.S. Cl. .................................. 564/212; 548/215; 548/237; 549/512; 549/513; 549/523; 549/529; 549/554; 549/555; 549/560; 564/211

[58] Field of Search ................ 564/212, 211; 548/215, 548/237; 549/560, 554, 555, 512, 513, 523, 529; 514/374, 628, 630

[56] References Cited

U.S. PATENT DOCUMENTS

| | | | |
|---|---|---|---|
| 4,235,892 | 11/1980 | Nagabhushan | 424/221 |
| 4,311,857 | 1/1982 | Nagabhushan | 564/212 |
| 4,361,557 | 11/1982 | Nagabhushan | 424/226 |
| 4,743,700 | 5/1988 | Jommi et al. | 548/216 |
| 4,876,352 | 10/1989 | Schumacher et al. | 548/232 |

FOREIGN PATENT DOCUMENTS 07608  5/1992  World Int. Prop. O. .......... 564/212

OTHER PUBLICATIONS

Clark et al, *Synthesis*, pp. 891–894 (1991).
Schumacher, et al, *J. Org. Chem.*, 55, pp. 5291–5294 (1990).
McCombie, et al, *Tet. Lett.*, 28, pp. 5395–5398 (1987).
Tyson, *Chem. and Indust.*, pp. 118–122 (1988).

*Primary Examiner*—Shailendra Kumar
*Attorney, Agent, or Firm*—Paul A. Thompson

[57] ABSTRACT

The present invention comprises a process for the asymmetric synthesis of florfenicol, thiamphenicol or chloramphenicol, from a derivative of trans-cinnamic acid, comprising the steps:

(a) converting the acid to an acid chloride using a chlorinating agent, and reducing the acid chloride to a trans allylic alcohol with a reducing agent;

(b) asymmetrically epoxidizing the allylic alcohol of step (a), by reacting with t-butylhydroperoxide in the presence of a chiral epoxidation catalyst prepared from titanium (IV) isopropoxide and L-diisopropyltartaric acid, to form a chiral epoxide;

(c) regioselectively opening the epoxide of step (b) by sequentially treating with sodium hydride, zinc chloride and dichloroacetonitrile to form an oxazoline;

(d) stereoselective inversion/isomerization of the oxazoline of step (c) by sequentially treating with: (i) a lower alkylsulfonyl chloride and a tertiary amine base; (ii) sulfuric acid and water; (iii) an alkali metal hydroxide; to form an oxazoline;

(e) optionally treating the oxazoline of step (d) with a fluorinating agent, for preparing florfenicol, then hydrolyzing with acid.

In an alternative embodiment, the present invention comprises a process for isomerizing of the S,S-isomer of florfenicol to the R,S-isomer (I) by sequentially treating with: (i) a lower alkylsulfonyl chloride and a tertiary amine base; (ii) sulfuric acid and water; (iii) an alkali metal hydroxide.

The present invention further comprises a process for regioselectively opening an epoxide to form a threo-oxazoline.

9 Claims, No Drawings

ASYMMETRIC PROCESS FOR PREPARING FLORFENICOL, THIAMPHENICOL CHLORAMPHENICOL AND OXAZOLINE INTERMEDIATES

The present invention relates to a stereospecific process for preparing florfenicol, thiamphenicol and chloramphenicol having the correct relative and absolute stereochemistry from achiral starting materials. The present invention also relates to a process for isomerizing the R,R-enantiomer of florfenicol to florfenicol having the proper R,S stereochemistry. In addition, the present invention relates to a stereospecific process for preparing oxazoline intermediates useful in the synthesis of florfenicol, thiamphenicol, chloramphenicol, and related antibiotics.

BACKGROUND OF THE INVENTION

Florfenicol (I) is a broad spectrum antibiotic having activity against Gram positive, Gram negative and thiamphenicol-resistant bacteria, as disclosed in U.S. Pat. No. 4,235,892.

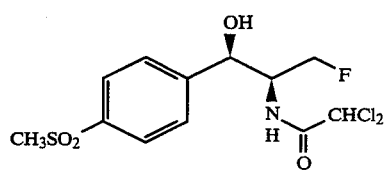

Thiamphenicol (IX) and chloramphenicol (X) are structurally related antibiotics known in the art.

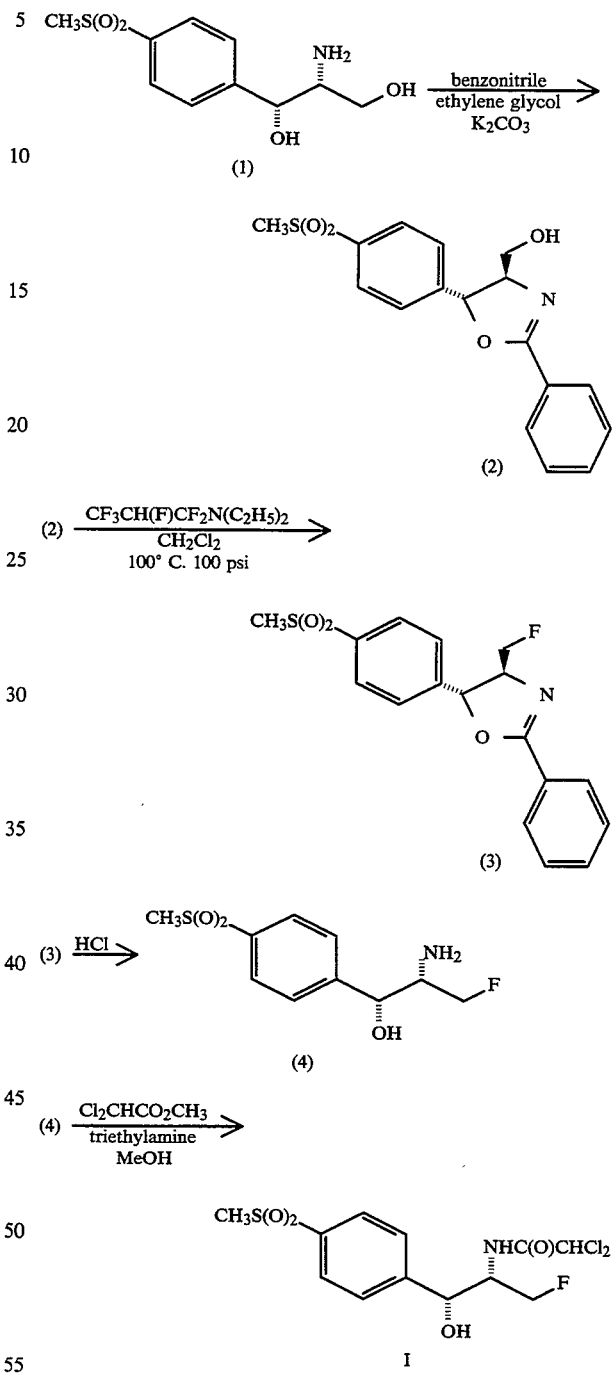

Several approaches to the synthesis of florfenicol have been reported, e.g. Tyson, *Chem Ind.*, (1988) pp. 118–122; and U.S. Pat. No. 4,743,700. However, these processes typically suffer from low overall yields and require either a resolution step or expensive chiral starting materials.

Schumacher et al., *J. Org. Chem.*, 18 (1990) pp. 5291–5294, describes a synthesis of florfenicol starting from a commercially available chiral starting material, e.g. compound (1). Compound (1) is converted to the oxazoline (2), to protect the secondary hydroxyl group, and (2) is converted to the fluoride (3). The oxazoline protecting group is removed by treatment with acid and the resulting amino-alcohol (4) converted to florfenicol I. However, the Schumacher et al. process again requires the use of expensive chiral starting materials.

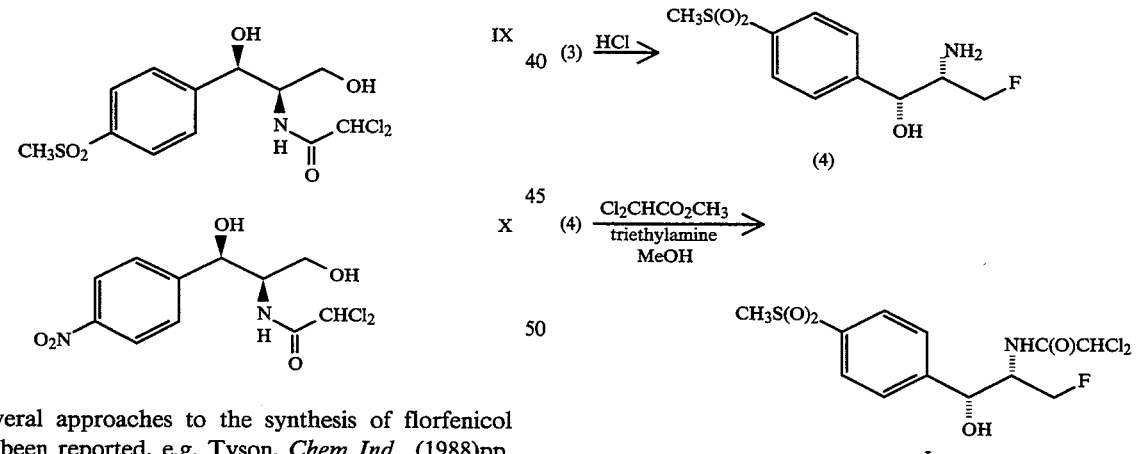

Clark et al., in *Synthesis,* (1991) pp. 891–894, disclose a process for the synthesis of florfenicol via the stereoselective hydrolysis of ethyl D,L-threo-3-(4-methyl-thiophenyl)-serinate hydrochloride (5) using enzymes to give (2S,3R)-3-(4-methyl-thiophenyl)serine (7) and the unreacted ester ethyl (2R.3S)-3-(4-methyl-thiophenyl)serinate hydrochloride (6). The acid (7), and the ester (6), are then converted via alternative multi-step sequences to the R,R-oxazoline (2). Compound (2) is then converted to florfenicol by the process of Schumacher et al., described above.

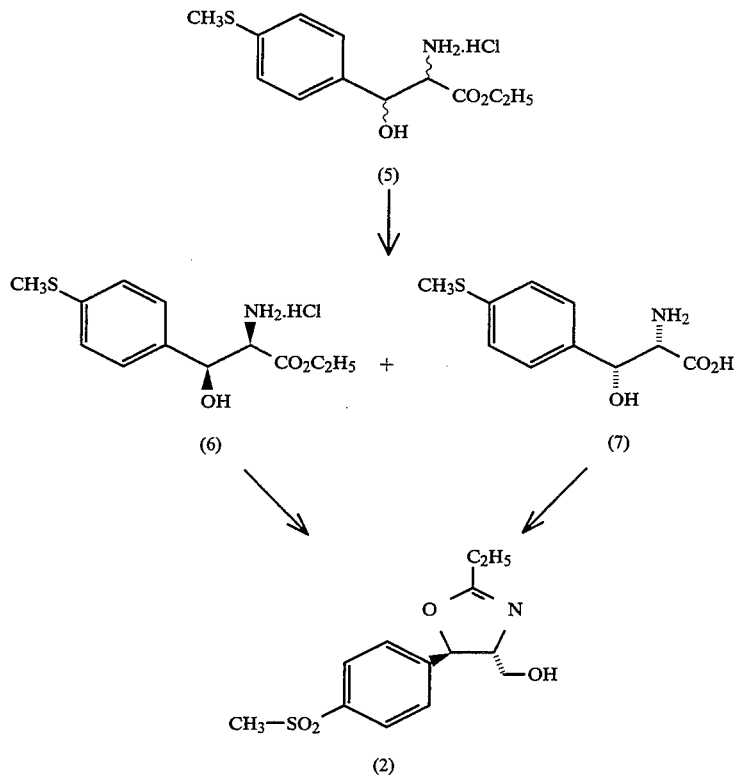

The Clark et al. process, while avoiding the use of expensive chiral starting materials, is chemically inefficient, producing a mixture of chiral ester (6) and acid (7) which must be separately converted to (2). Thus, the prior art does not teach a chemically efficient stereoselective process for the synthesis of florfenicol that avoids the use of expensive chiral precursors.

SUMMARY OF THE INVENTION

The present invention involves a process for the asymmetric synthesis of florfenicol, thiamphenicol or chloramphenicol from a trans cinnamic acid derivative of the formula

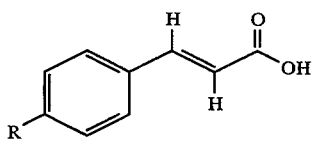

wherein R is nitro or methanesulfonyl, comprising the steps:
  (a) converting the acid to an acid chloride using a chlorinating agent, and reducing the acid chloride to a trans allylic alcohol with a reducing agent;
  (b) asymmetrically epoxidizing the allylic alcohol of step (a), by reacting with t-butylhydroperoxide in the presence of a chiral epoxidation catalyst prepared from titanium (IV) isopropoxide and L-diisopropyltartaric acid, to form an epoxide of the formula

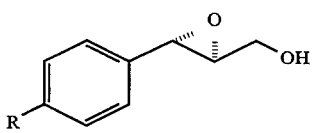

wherein R is as defined above;
  (c) regioselectively opening the epoxide of step (b) by sequentially treating with a strong base, a Lewis acid and dichloroacetonitrile to form an oxazoline of the formula

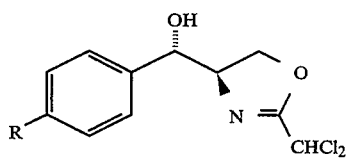

wherein R is as defined above;
  (d) stereoselective inversion/isomerization of the oxazoline of step (c) by sequentially treating with: (i) a lower alkylsulfonyl chloride and a tertiary amine base; (ii) sulfuric acid and water; and (iii) an alkali metal hydroxide; to form an oxazoline of the formula

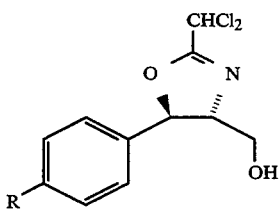

wherein R is as defined above; and
(e) either:
  (i) wherein R is methanesulfonyl, treating the oxazoline of step (d) with a fluorinating agent, then hydrolyzing the oxazoline with acid to obtain florfenicol; or
  (ii) hydrolyzing the oxazoline of step (d) with acid to obtain:
     (a) wherein R is methanesulfonyl, thiamphenicol; or
     (b) wherein R is nitro, chloramphenicol.

Preferred is a process as described above wherein the chlorinating agent of step (a) is thionyl chloride, the reducing agent of step (a) is $NaBH_4$, the lower alkylsulfonyl chloride of step (d) is MsCl, the tertiary amine base of step (d) is triethylamine, the alkali metal hydroxide of step (d) is NaOH, the fluorinating agent of step (e) is $CF_3CH(F)CF_2N(C_2H_5)_2$, and the acid of step (e) is AcOH.

More preferred is a process as described above wherein the strong base of step (c) is an alkali metal hydride, preferably sodium hydride, and the Lewis acid of step (c) is zinc chloride.

In an alternative embodiment, the process of the instant invention comprises the isomerization of the S,S-isomer of florfenicol to the R,S-isomer (I) by sequentially treating with: (i) a lower alkylsulfonyl chloride and a tertiary amine base; (ii) sulfuric acid and water; (iii) an alkali metal hydroxide.

In a third embodiment the process of present invention comprises a process for regioselectively opening an epoxide of the formula

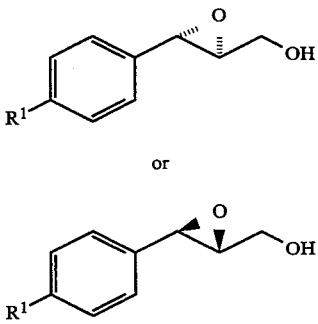

or wherein $R^1$ is methanesulfonyl, nitro or hydrogen by sequentially treating with a strong base, a Lewis acid and dichloroacetonitrile to form a threo-oxazoline of the formula

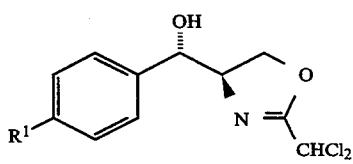

or

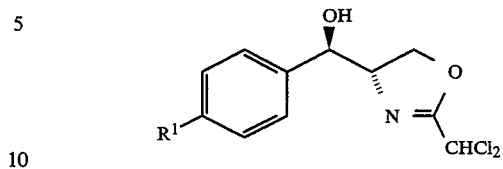

respectively, wherein $R^1$ is as defined above. The epoxide opening process can be carried out on chiral (as shown) or racemic starting materials. Where chiral starting materials are used the reaction is both regio- and stereo-selective, producing chiral oxazolines.

Preferred is a process for preparing an oxazoline as described above wherein the strong base is an alkali metal hydride, preferably sodium hydride, and the Lewis acid is zinc chloride.

The process of the present invention does not suffer the shortcomings of the prior art processes. It is chemically efficient, proceeds in high yield, and avoids the problems of expensive chiral starting materials by utilizing a reusable chiral auxiliary to introduce optical activity.

DETAILED DESCRIPTION

As used herein:

"fluorinating agent" is a reagent or combination of reagents capable of converting a primary alcohol to the analogous fluoride. Preferred fluorinating agents include: α,α-difluoroalkylamine fluorinating agents disclosed in U.S. Pat. No. 4,876,352, such as N-(1,1,2,3,3,3-hexafluoropropyl)diethylamine; HF; phosphorous fluorides; 2-chloro-1,1,2-trifluorotriethylamine; and inorganic fluoride, such as LiF, in a polyol solvent. Most preferred is N-(1,1,2,3,3,3-hexafluoropropyl)diethylamine.

"lower alkyl" means a saturated hydrocarbon chain having from 1–6 carbon atoms, the chain being straight or branched;

"alkali metal hydroxide" means sodium, lithium or potassium hydroxide, preferably NaOH;

"strong base" means a strong nonaqueous base selected from the group consisting of alkali metal hydride, alkali metal alkoxide and lower alkyllithium;

"alkali metal hydride" means sodium, lithium or potassium hydride, preferably sodium hydride;

"alkali metal alkoxide" means an alkali metal salt of a lower alkyl alcohol. Preferred alkali metal alkoxides are alkali metal methoxides, ethoxides, iso-propoxides and tert-butoxides. Most preferred are potassium t-butoxide, potassium methoxide, sodium methoxide and sodium ethoxide.

"lower alkyllithium" is an alkyllithium selected from n-butyllithium, sec-butyllithium and tert-butyllithium;

"Lewis acid" means an inorganic salt selected from the group consisting of zinc chloride, magnesium chloride and manganese chloride;

"chlorinating agent" is a reagent capable of converting a carboxylic acid to the analogous acid chloride, such as $SOCl_2$ or oxalyl chloride, and is preferably $SOCl_2$; and "reducing agent" is a reagent which can convert a conjugated acid chloride to an allylic alcohol, such as $NaBH_4$ or sodium cyanoborohydride, and is preferably $NaBH_4$.

As used herein the following reagents are identified by the indicated abbreviations: dimethylsulfide (DMS); diisopropyl L-tartaric acid (L-DIPT); tetrahydrofuran (THF); ethyl acetate (EtOAc); methyl isobutylketone (MIBK); methanesulfonyl chloride (MsCl); ethanol (EtOH); acetic acid (AcOH).

In one aspect, designated Method A, the process of the present invention involves the conversion of a para-R-substituted derivative of E-cinnamic acid, wherein the substituent R is nitro or methanesulfonyl, to florfenicol, thiamphenicol or chloramphenicol according to Reaction Scheme A. The process is stereospecific, producing florfenicol, thiamphenicol or chloramphenicol having the requisite absolute stereochemistry, e.g. R,S for florfenicol, and R,R for thiamphenicol and chloramphenicol.

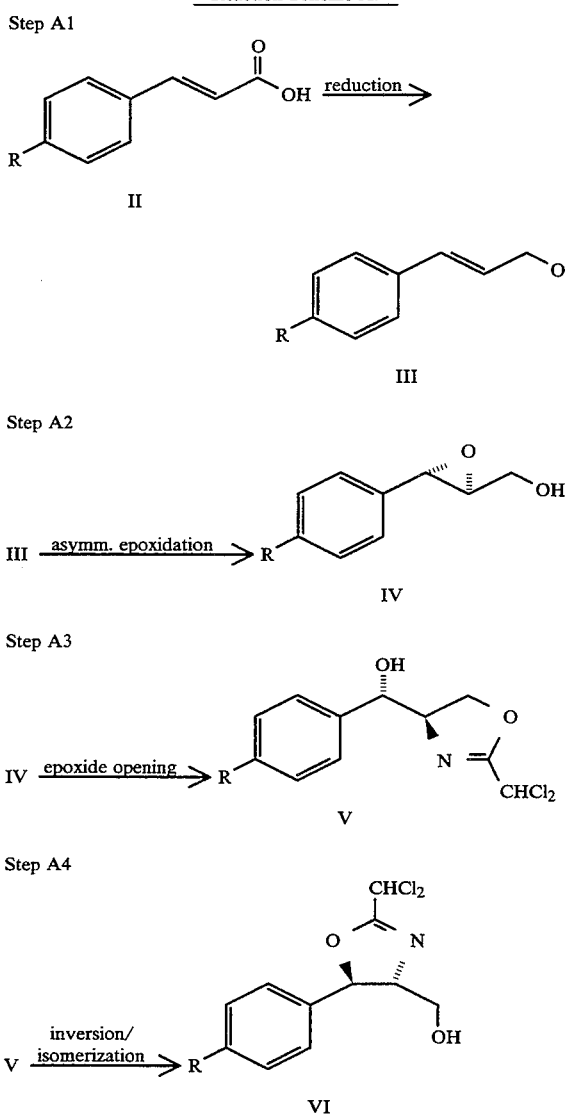

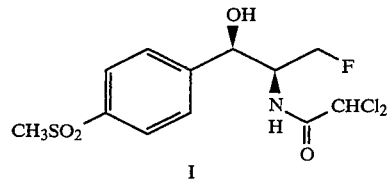

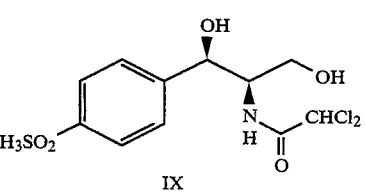

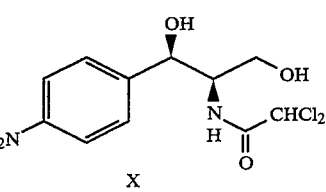

In Method A, step A1, the E-cinnamic acid derivative II is reacted with a chlorinating agent, such as $SOCl_2$, in the presence of a suitable solvent, e.g. $CH_2Cl_2$, at reflux temperature for a period of 30 to 90 min., preferably about 1 h., to form the analogous acid chloride. The acid chloride is treated with a reducing agent, such as $NaBH_4$, in an alcohol solvent, e.g. EtOH, at $-10°$ to $+25°$ C., preferably at $-5°$ to $+10°$ C., for a period of 30 to 90 min., preferably about 1 h., followed by quenching in a mixture of ice/water and a suitable acid, such as HCl, and isolating the product E-allylic alcohol III by extracting with $CH_2Cl_2$.

In step A2, the E-allylic alcohol (III) of step A1 is epoxidized using the so-called "Sharpless epoxidation", as described by Sharpless, et al. in *J. Amer. Chem. Soc.,* 102, (1980) 5974. The Sharpless catalyst is prepared by combining equimolar amounts of L-DIPT and titanium (IV) isopropoxide in the presence of 4Å molecular sieves, and stirring at about $-20°$ C. for about ½ h. The allylic alcohol of step A1, as a solution in $CH_2Cl_2$, and a 3M solution of t-butyl-hydroperoxide in 2,2,4-trimethylpentane are slowly added, preferably in a dropwise manner, to the catalyst mixture at about $-20°$ C. and reacted for 2 to 6 h., preferably about 4 h. The mixture is quenched by adding DMS, followed by filtration, treatment of the filtrate with a saturated solution of NaF in water at room temperature for about 16 h., a second filtration employing a filter aid, such as Celite ®, and extraction of the filtrate with $CH_2Cl_2$ to isolate the R,R-isomer (IV) of the epoxide product, having high optical purity.

In step A3, the epoxide IV of step A2, as a solution in a suitable solvent, such as THF, is slowly added, preferably in a dropwise manner, to a suspension of NaH in THF at 0° to 10° C., preferably about 5° C., and reacted at 0° to 10° C., preferably about 5° C., for about ½ h. A solution of anhydrous $ZnCl_2$ in THF is added to the cold mixture thus obtained. After about ½ h. at 0° to 10° C., preferably about 5° C., a solution of dichloroacetonitrile in THF is added, along with 4Å molecular sieves, and the mixture maintained at about 5° C. for about 15 min., then heated to 50° to 60° C., preferably about 55° C. for about 16 h. The resulting mixture is cooled to room temperature, quenched by adding an aqueous solution of NaHCO3, and extracted with a suitable solvent, such as EtOAc to give the crude product, which is slurried isopropanol, followed by filtration and drying to isolate the chiral oxazoline V.

In step A4, the oxazoline V of step A3 is combined with a trialkylamine, preferably triethylamine, and pyridine at room temperature. The mixture is cooled to 0°–10° C., preferably about 5° C., and an alkylsulfonyl chloride, preferably MsCl, is slowly added (preferably in a dropwise manner) to the mixture, which is stirred at 0°–10° C., preferably about 5° C., for about 2 hours. The pH of the mixture is adjusted to 1.9 to 4.0, preferably about 2.0, by addition of an aqueous acid, preferably H2SO4, and most preferably 3.0N H2SO4. THF is added to generate a homogeneous mixture. After warming to room temperature for 10 min., the mixture is treated with an alkali metal hydroxide, preferably NaOH, and most preferably administered as 50% NaOH (aqueous), to bring the pH to >9.5, preferably about 12.5. Concentration of the mixture, and extraction with a suitable solvent, such as EtOAc, gave the isomerized oxazoline product VI.

In step A5(i), for preparing florfenicol, the isomerized oxazoline VI, wherein R is methanesulfonyl, of step A4 is fluorinated via the process disclosed in U.S. Pat. No. 4,876,352, then hydrolyzed by treating with acid. The fluorination is preferably carried out by treating the oxazoline VI with N-(1,1,1,2,3,3-hexafluoropropyl)-diethylamine in a suitable solvent, e.g. CH2Cl2, in a bomb at a temperature of about 110° C. The hydrolysis of the resulting fluoro-oxazoline intermediate is preferably carried out by addition of 1N H2SO4, aqueous, to adjust the pH to 6.5–6.0, then by addition of AcOH to further acidify the mixture to a pH of about 5.5–5.0.

In steps A5(iia) and A5(iib), for preparing thiamphenicol or chloramphenicol, respectively, the isomerized oxazoline VI of step A4 is hydrolyzed by treating with acid to produce: (a) wherein R is methanesulfonyl, thiamphenicol; or (b) wherein R is nitro, chloramphenicol. The hydrolysis of the oxazoline is preferably carried out by addition of 1N H2SO4, aqueous, to adjust the pH to 6.5–6.0, then by addition of AcOH to further acidify the mixture to a pH of about 5.5–5.0.

Starting compounds of formula II can be prepared via methods well known to those skilled in the art, e.g. the procedure of Preparation I (described below).

In another alternative aspect, Method B, the present invention is a process, as outlined in Reaction Scheme B, for converting the S,S-isomer of florfenicol (VII), [prepared from the epoxide IV of Method A, step A2. via the method of McCombie et al, as disclosed in *Tet. Lett.,* 28, (1987) 5395], to the correct R,S-isomer I. The isomerization is stereospecific and proceeds via an oxazoline intermediate VIII, which is not isolated but converted directly to florfenicol I.

Reaction Scheme B:

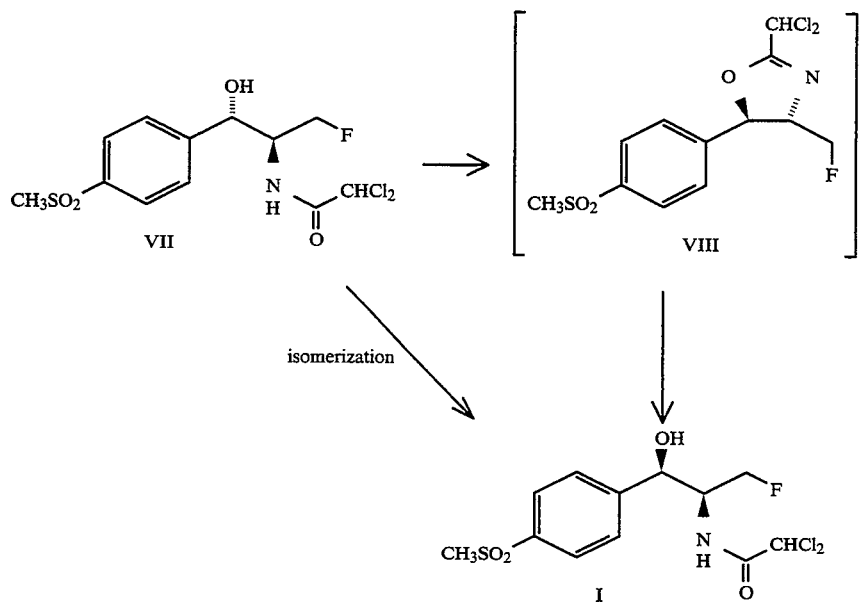

The isomerization of Method B is carried out using a procedure similar to that described in Method A, step A4. The S,S isomer of florfenicol is combined with a trialkylamine, preferably triethylamine, and pyridine at room temperature. The mixture is cooled to 0°–10° C., preferably about 5° C., and an alkylsulfonyl chloride, preferably MsCl, is slowly added (preferably in a dropwise manner) to the mixture, which is stirred at 0°–10° C., preferably about 5° C., for about 2 hours. The mixture is treated with an alkali metal hydroxide, preferably NaOH, and most preferably administered as 50% NaOH (aqueous), to bring the pH to about 12.5 to form an oxazoline intermediate VIII. The oxazoline VIII is treated with an aqueous solution of an acid, such as HOAc, at room temperature to give the correct R,S-isomer of florfenicol I.

In a third aspect, Method C, the present invention is a process, as outlined in Reaction Scheme C, for regioselectively opening an epoxide of the formula XI, wherein $R^1$ is as defined above, to form an oxazoline of the formula XII, wherein $R^1$ is as defined above. The process is regiospecific, producing oxazoline products.

In contrast, the prior art teaches opening of epoxides XI to occur via attack at the benzylic carbon atom.

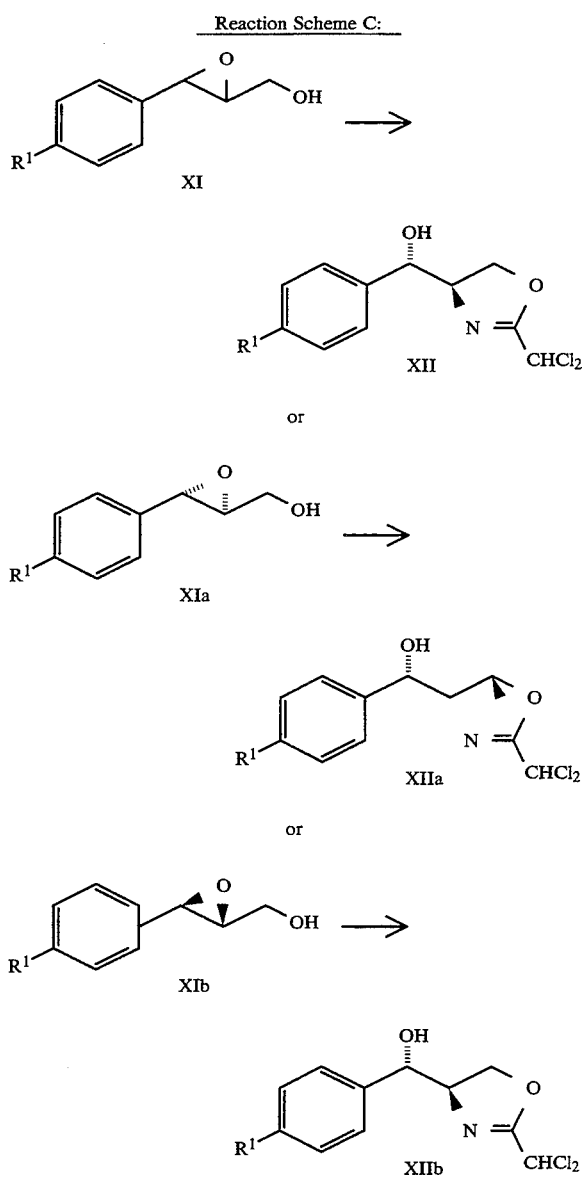

(The stereochemistry indicated in compound XII is intended to reflect relative stereochemistry only. However, where a chiral epoxide, e.g. XIa or XIb is used, the oxazoline stereochemistry represents both relative and absolute stereochemistry as shown in compounds XIIa and XIIb.)

The epoxide opening of Method C is carried out via the procedure described in Method A, step A3.

The following preparations and examples are illustrative of the process of the present invention:

Preparation 1

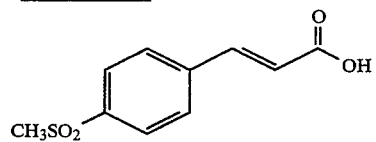

-continued
Preparation 1

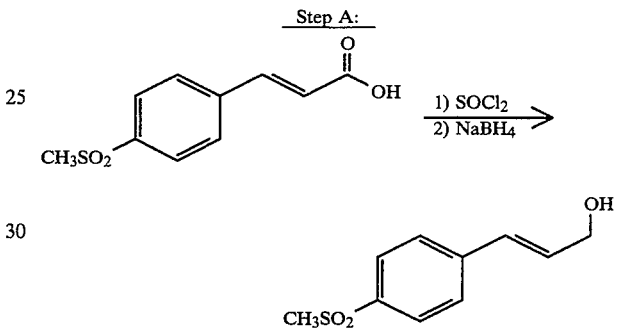

Combine 312 g (2.99 mole) of malonic acid, 506 mL of pyridine, 30 mL of piperidine and 300 g (1.49 mole) of p-methylsulfonyl-benzaldehyde and heat the mixture to 95°–100° C. for 4 h. Cool the mixture to room temperature and slowly pour into 3 L of a mixture of HCl, water and ice. Collect the resulting precipitate by filtration and dry the solid to give 340 g (83% yield) of the E-cinnamic acid derivative, m.p.=294°–296° C. $^1$H NMR (DMSO-d$_6$, ppm): 7.96 (s, 4H); 7.78 (d, J=16 Hz, 1H); 6.71 (d, J=16 Hz, 1H); 3.5 (br. s, 1H); 3.25 (s, 3H).

Step A:

Combine 96 mL (1.35 mole) of SOCl$_2$ and 50 g (0.225 mole) of the product of Preparation 1 and heat the mixture at reflux for 1 hour. Distill off the excess SOCl$_2$, then add 100 mL of CH$_2$Cl$_2$. Add the resulting solution (dropwise) to a precooled (−5° C.) mixture of 42 g (1.1 mole) of NaBH$_4$ and 500 mL of EtOH. Stir the mixture for 1 h. at 10° C., then quench by pouring into a mixture of HCl, water and ice. Extract with CH$_2$Cl$_2$ (3×300 mL), combine the extracts, concentrate and filter to give 28 g (74% yield) of the product allylic alcohol, m.p.=126°–127° C. $^1$H NMR (CDCl$_3$, ppm): 7.85 (d, J=9 Hz, 2H); 6.52 (d of t, J=16 Hz, 5 Hz, 1H); 4.38 (d of d, J=5 Hz, 1 Hz, 2H); 3.05 (s, 3H); 1.93 (br. s, 1H).

Step B

Combine 8 g of 4Å molecular sieves, 1.74 g (7.4 mmol) of L-DIPT and 2.16 g (7.4 mmol) of titanium (IV) isopropoxide at −20° C. under anhydrous conditions, and stir for 30 min. Add (dropwise) a solution of 8.1 g (37 mmol) of the allylic alcohol of step A in 500 mL of CH$_2$Cl$_2$, and 13.4 mL of a 3.0M solution of t- butyl hydroperoxide in 2,2,4-trimethylpentane. Stir the mixture at −20° C. for 4 h., then quench by adding 6.0 mL of DMS. Filter the mixture, then add 250 mL of saturated NaF (aqueous) to the filtrate and stir for 16 h. at 25° C. Filter through Celite®, and extract the filtrate with $CH_2Cl_2$ (3×100 mL). Combine the extracts and wash with water (2×100 mL), then concentrate the extracts and filter to obtain 7.15 g (82% yield) of the S,S-epoxide, having an optical purity of 97% e.e. and m.p.=104°-106° C. $^1$H NMR (CDCl$_3$): 7.92 (d, J=8 Hz, 2H); 7.49 (d, J=8 Hz, 2H); 4.10 (d of d, J=17 Hz, 3 Hz, 1H 4.04 (s, 1H); 3.85 (d of d, J=17 Hz, 3 Hz, 1H); 3.20–3.17 (m, 1H); 3.05 (s, 3H): 1.88 (br. s, 1H). The optical purity of the epoxide is determined by chiral HPLC (Chiracel® OJ 25 cm×4.6 mm id column. 25° C., 1:1 hexane/isopropanol containing 1% acetonitrile).

Step C

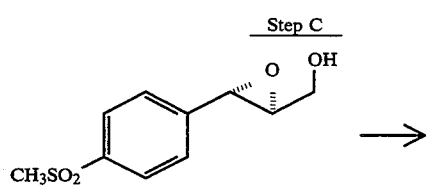

Combine 6.1 g (153 mmol) of NaH (60% dispersion in oil) and 90 mL of THF and cool the resulting suspension to 5° C. Add (dropwise) a solution of 30 g (128 mmol) of the epoxide of step B in 300 mL of THF, then stir the mixture at 5° C. for 30 min. Add (dropwise) 17.8 g (128 mmol) of anhydrous $ZnCl_2$ as a solution in 250 mL of THF, and stir at 5° C. for 30 min. Add (dropwise) 17.0 g (153 mmol) of $CHCl_2CN$ as a solution in 10 mL of THF, then add 1 g of 4Å molecular sieves and continue stirring at 5° C. for 15 min. Heat the mixture to 55° C., stir for 16 h., then cool to room temperature and quench with $NaHCO_3$ (aqueous). Extract with EtOAc (4×400 mL), combine the extracts and concentrate to a residue. Slurry the residue in isopropanol, filter and dry the solid to obtain 16.0 g of the oxazoline. The oxazoline is recrystallized from MIBK to obtain purified oxazoline (97% purity), m.p.=156.5°-157.5° C. $^1$H NMR (CDCl$_3$): 7.93 (d, J=8.4 Hz, 2H); 7.60 (d, J=8.4 Hz, 2H); 6.26 (s, 1H); 5.14 (d, J=4 Hz, 1H); 4.57 (d of d of d, J=8.7 Hz, 7.9 Hz, 4.0 Hz, 1H); 4.46 (d of d, J=9.7 Hz, 7.9 Hz, 1H); 4.28 (d of d. J=9.7 Hz, 8.7 Hz, 1H); 3.05 (s, 3H); 2.60 (br. s, 1H).

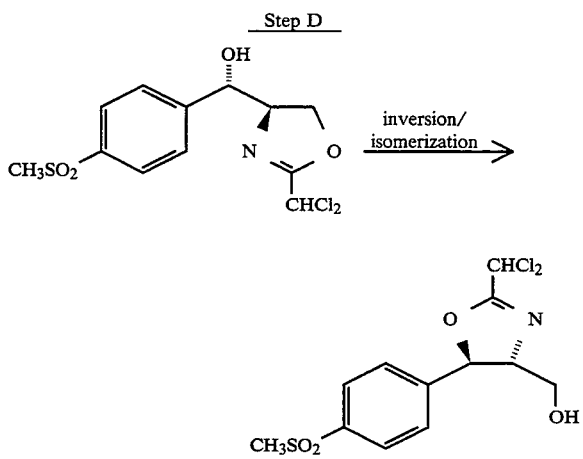

Combine 3.5 g (10 mmol) of the oxazoline of step C, 5 mL of pyridine and 2.8 mL of triethylamine at 25° C., cool the mixture to 5° C. and add (dropwise) 0.95 mL (12 mmol) of MsCl. Stir the mixture at 5° C. for 2 h., then add 3.0N $H_2SO_4$ (aqueous) to adjust the pH to 2. Add 5 mL of THF, warm the mixture to room temperature and stir for 10 min. Add 50% NaOH (aqueous) to adjust the pH to 12.5. Concentrate the mixture and extract with EtOAc (3×40 mL). Combine the extracts and concentrate to give the product, having an optical purity of >99.9% and m.p.=144°-145° C. $^1$H NMR (DMSO-d$_6$): 8.00 (d, J =8.3 Hz, 2H); 7.26 (s, 1H); 7.60 (d, J=8.3 Hz, 2H); 5.75 (d, J=6.4 Hz, 1H); 5.18 (t, J=5.6 Hz 1H); 4.10–4.05 (m, 1H); 3.75–3.65 (m, 1H); 3.60–3.55 (m, 1H); 3.23 (s, 3H). The optical purity of the oxazoline is determined by chiral HPLC (Chiracel® OJ 25 cm×4.6 mm id column, 25° C., 69:30:1 hexane/isopropanol/acetonitrile).

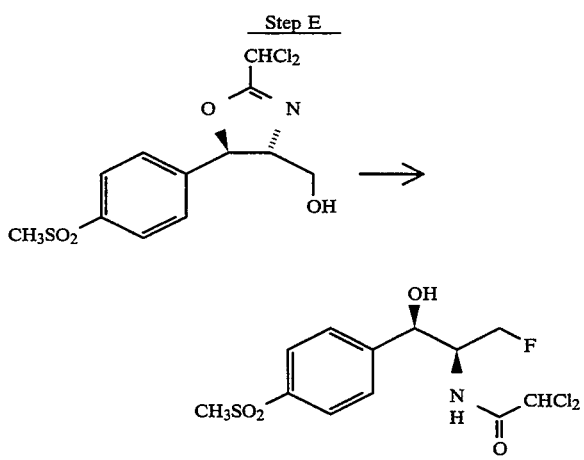

The oxazoline of step D is fluorinated according to the method disclosed in U.S. Pat. No. 4,876,352. The resulting fluoro oxazoline is then hydrolyzed by treating with 1N $H_2SO_4$, then with HOAc, using the procedure of Example 2.

Example 2

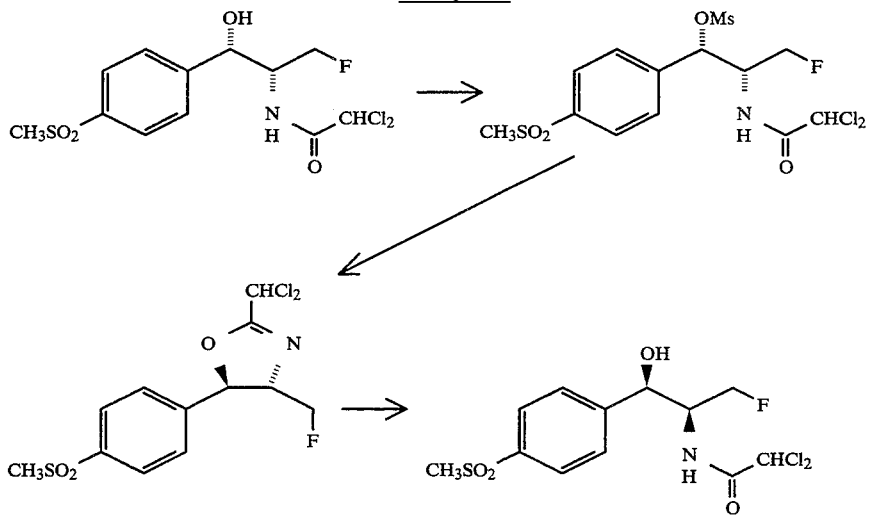

Combine 3.0 g (8.4 mmol) of the S,S-isomer of florfenicol, 3 mL of THF, 3 mL of pyridine and 2.3 mL of triethylamine, then stir while cooling to 10°–15° C. Slowly add (dropwise) a solution of 1.9 g (16.8 mmol) of MsCl in 2 mL of THF to the stirred mixture, maintaining the temperature at 10°–15° C. Stir the resulting mixture at 10° C. for 30 min., then warm to room temperature and stir for 1 h., at which point formation of the mesylate intermediate is complete. Add 10 mL of water to the mixture, cool to 10° C., then slowly add (dropwise) a solution of 2.7 g of 50% NaOH (aqueous) diluted in 5 mL of water. Stir at 10° C. for 10 min., then add an additional 0.5 g of 50% NaOH and continue stirring for 10 min. more, to complete formation of the oxazoline intermediate. Add 1.0N H$_2$SO$_4$ (aqueous) to the mixture to adjust the pH to 6.5–6.0, then further acidify by adding HOAc until the pH reaches 5.5–5.0, at which point a precipitate forms. Add acetone to dissolve the precipitate and stir the mixture at room temperature for 16 h. Concentrate the mixture in vacuo to remove the THF, pyridine and acetone, then stir the resulting mixture for 30 min. at room temperature. Filter and dry the solid to give the product florfenicol, 2.5 g, having the correct relative and absolute stereochemistry.

We claim:

1. A process for the asymmetric synthesis of florfenicol, thiamphenicol or chloramphenicol from a trans cinnamic acid derivative of the formula

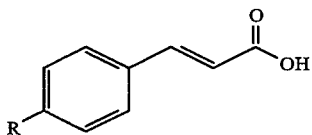

wherein R is nitro or methanesulfonyl, comprising the steps:
(a) converting the acid to an acid chloride using a chlorinating agent, and reducing the acid chloride to a trans allylic alcohol with a reducing agent;
(b) asymmetrically epoxidizing the allylic alcohol of step (a), by reacting with t-butylhydroperoxide in the presence of a chiral epoxidation catalyst prepared from titanium (IV) isopropoxide and L-diisopropyltartaric acid, to form an epoxide of the formula

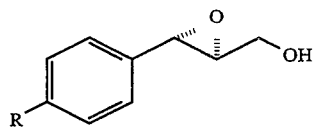

wherein R is as defined above;
(c) regioselectively opening the epoxide of step (b) by sequentially treating with a strong base, a Lewis acid and dichloroacetonitrile to form an oxazoline of the formula

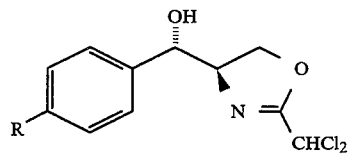

wherein R is as defined above;
(d) stereoselective inversion/isomerization of the oxazoline of step (c) by sequentially treating with: (i) a lower alkylsulfonyl chloride and a tertiary amine base; (ii) sulfuric acid and water; and (iii) an alkali metal hydroxide; to form an oxazoline of the formula

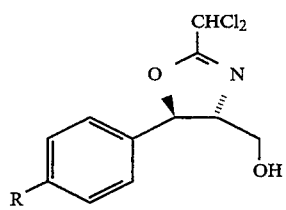

wherein R is as defined above; and
(e) either:
 (i) wherein R is methanesulfonyl, treating the oxazoline of step (d) with a fluorinating agent, then hydrolyzing the oxazoline with acid to obtain florfenicol; or (ii) hydrolyzing the oxazoline of step (d) with acid to obtain:
(a) wherein R is methanesulfonyl, thiamphenicol; or
(b) wherein R is nitro, chloramphenicol.

2. The process of claim 1 wherein the strong base of step (c) is an alkali metal hydride and the Lewis acid of step (c) is zinc chloride.

3. The process of claim 2 wherein: the chlorinating agent of step (a) is thionyl chloride; the reducing agent of step (a) is NaBH$_4$; the alkali metal hydride of step (c) is NaH; the lower alkylsulfonyl chloride of step (d) is MsCl; the tertiary amine base of step (d) is triethylamine; the alkali metal hydroxide of step (d) is NaOH; the fluorinating agent of step (e) is CF$_3$CH(F)CF$_2$N(C$_2$H$_5$)$_2$; and the acid of step (e) is AcOH.

4. The process of claim 3 wherein: in step (c) the treatment of the epoxide with NaH and ZnCl$_2$ is carried out in THF at a temperature of 0° to 10° C., and the treatment with dichloroacetonitrile is carried out first at 0° to 10° C., then at 50° to 60° C.; and in step (d) the treatment with MsCl and triethylamine is carried out in pyridine at 0° to 10° C.; the sulfuric acid and water is a 3N solution of H$_2$SO$_4$ in water; and the NaOH is a 50% solution of NaOH in water.

5. The process of claim 4 wherein in step (d) sufficient 3N H$_2$SO$_4$ is used to adjust the pH to 1.9 to 4.0, and sufficient 50% NaOH is used to adjust the pH to >9.5.

6. A process for preparing florfenicol, comprising the isomerization of the S,S-isomer of florfenicol to the R,S-isomer (I) by sequentially treating with: (i) a lower alkylsulfonyl chloride and a tertiary amine base; (ii) sulfuric acid and water; and (iii) an alkali metal hydroxide.

7. A process for regioselectively opening an epoxide of the formula

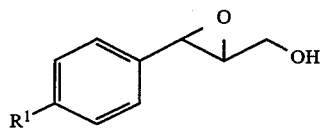

wherein R$^1$ is methanesulfonyl, nitro or hydrogen by sequentially treating with a strong base, a Lewis acid and dichloroacetonitrile, to form an oxazoline of the formula

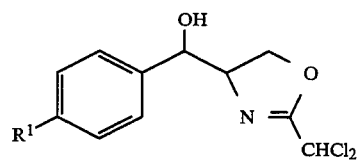

having threo relative stereochemistry, wherein R$^1$ is as defined above.

8. The process of claim 7 wherein the strong base is an alkali metal hydride and the Lewis acid is zinc chloride.

9. The process of claim 8 wherein the alkali metal hydride is NaH, the treatment of the epoxide with NaH and ZnCl$_2$ is carried out in THF at a temperature of 0° to 10° C., and the treatment with dichloroacetonitrile is carried out first at 0° to 10° C., then at 50° to 60° C.

* * * * *